United States Patent [19]

Kaivola

[11] 4,198,966

[45] Apr. 22, 1980

[54] INTRAUTERINE CONTRACEPTIVE AND METHOD OF MANUFACTURING THE SAME

[76] Inventor: Seppo Kaivola, Linnanherantie 3B, 00950 Helsinki 95, Finland

[21] Appl. No.: 930,187

[22] Filed: Aug. 2, 1978

[30] Foreign Application Priority Data

Jun. 29, 1978 [FI] Finland .................................. 782102

[51] Int. Cl.² .............................................. A61F 5/46
[52] U.S. Cl. .................................................... 128/130
[58] Field of Search ........................ 128/130, 127, 260

[56] References Cited

U.S. PATENT DOCUMENTS 3,952,734  4/1976  Van Os et al. .................... 128/130

*Primary Examiner*—Lawrence W. Trapp
*Attorney, Agent, or Firm*—Steinberg & Blake

[57] ABSTRACT

An intrauterine contraceptive device and method of manufacturing the same including a separately formed elongate body member including a lower body portion and an upper, reduced diameter body portion and a separately formed transversal member removably affixed to the upper end of the reduced diameter body portion. Prior to affixing the transversal member on the body member, a copper helical member is located over the reduced diameter body portion. A connecting member may be provided on the transversal member to facilitate connection thereof to the body member.

10 Claims, 5 Drawing Figures

INTRAUTERINE CONTRACEPTIVE AND METHOD OF MANUFACTURING THE SAME

BACKGROUND OF THE INVENTION

The intrauterine copper spiral or helical contraceptive devices presently in use are generally formed of a unitary plastic member comprising an elongated body portion and an integrally formed transversal portion formed at one of the body portion ends and projecting outwardly therefrom. In construction, such conventional spiral contraceptive devices are formed by winding copper wire around the entire body portion to form the spiral or helical component.

Such conventional copper spiral contraceptive devices are not entirely satisfactory since it is necessary during manufacture to wind the spiral or helical component onto the body portion. This manufacturing operation comprises a separate and distinct step in the overall manufacturing process and is time consuming.

Furthermore, in such conventional copper spiral intrauterine devices, the copper spiral is wound around the entire length of the body portion of the device despite the fact that the portion of the helix or spiral in the vicinity of the lower part of the body portion, i.e., that part of the body portion which is remote from the transversal portion, has little or no contraceptive effect. Despite the fact that such lack of contraceptive effect is known, prior art contraceptive devices of this type are formed with the copper helix or spiral along the entire body portion for reasons of ease in manufacture.

SUMMARY OF THE INVENTION

Accordingly, one object of the present invention is to provide a new and improved intrauterine contraceptive device of the copper spiral or helix type.

Another object of the present invention is to provide a new and improved method of manufacturing intrauterine contraceptive devices of the copper spiral or helix type.

Still another object of the present invention is to provide a new and improved intrauterine contraceptive device of the copper spiral type and a method for its manufacture wherein the copper spiral or helix is not separately wound around the body portion of the device and wherein the portion of the copper spiral is conveniently omitted from the lower part of the body portion.

Briefly, according to the present invention, these and other objects are attained by providing separately formed elongated body members, transversal members and copper spiral or helical members. Each body member is defined by a first, lower elongated cylindrical portion and a second, upper elongated reduced diameter cylindrical portion. The copper spiral member is located over the upper reduced diameter portion of the body member. Means are provided on the free end of the reduced diameter body portion for connecting the transversal member thereto.

DESCRIPTION OF THE DRAWINGS

A more complete appreciation of the invention and many of the attendant advantages thereof will be readily appreciated as the same becomes better understood by reference to the following detailed description when considered in connection with the accompanying drawings wherein.

DESCRIPTION OF THE PREFERRED EMBODIMENTS

Figure 1:
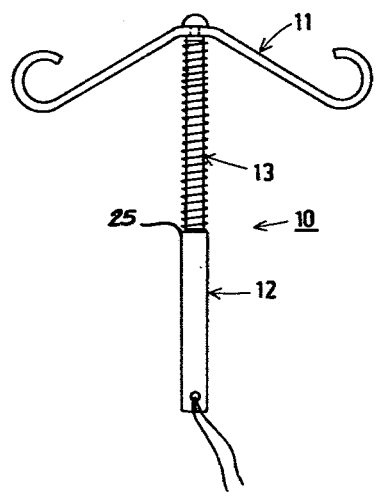
FIG. 1 is a side elevation view of the intrauterine contraceptive device of the present invention.
Figure 2:
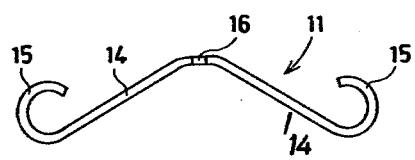
FIG. 2 is a side view of the transversal member comprising a part of the device of the present invention.
Figure 3:
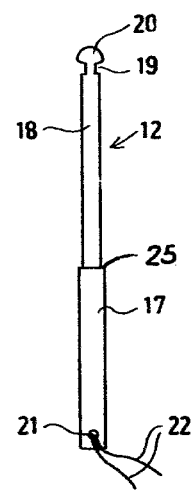
FIG. 3 is a side view of the body member comprising a part of the device of the present invention.

Referring now to the drawings wherein like reference characters designate identical or corresponding parts throughout the several views and more particularly to FIGS. 1-3, the intrauterine contraceptive device constructed in accordance with the present invention is generally denoted as 10 (FIG. 1). Referring to FIG. 2, a transversal member 11 is defined by a pair of leg portions 14 which are integrally joined at an apex to define a substantially V-shaped member. The free ends of each leg portion 14 terminate in upwardly curved pronglike portions 15. A bore 16 is formed through transversal member 11 at the apex defined by leg portions 14. According to the present invention, unlike the case in prior art devices, transversal members 11 are separately formed as shown in FIG. 2.

Also in accordance with the present invention, a plurality of elongated body members 12 are separately formed as seen in FIG. 3. Each body member 12 includes a lower elongated cylindrical portion 17 and an integrally formed upper body portion 18 of reduced diameter, i.e., which is thinner, with respect to lower body portion 17. An annular shoulder 25 is defined by the intersection of the lower and upper body portions 17, 18.

The free end or tip of upper body portion 18 has an annular groove 19 formed therein. An enlarged locking portion 20 is provided on the free end of upper body portion 18 above annular groove 19. A bore 21 is provided on the free end of lower body portion 17 through which thin wires 22 are passed as is conventional.

Further in accordance with the present invention, copper spiral or helix members 13 are separately formed. Thus, in the preferred embodiment, a suitable copper wire is formed into a continuous helical spiral such as by winding the wire around a mandrel and then cutting the formed spiral into spiral members 13 having an appropriate length. The gauge of the copper wire is preferably in the range from 0.4 to 0.6 mm. The surface area of the copper spiral or helix member 13 can therefore be about 350 $mm^2$ which is considerably greater than the surface area afforded by conventional spirals wherein the surface area usually is on the order of about 200 $mm^2$.

Transversal members 11 which are provided with the prong-like terminal ends 15 have a breadth of preferably between 15 and 25 mm. The length of the body members 12 is preferably between 30 and 40 mm.

The intrauterine contraceptive device 10 of the present invention is constructed as follows: The copper spiral member 13 is first located over the upper body portion 18 of body member 12 so that its lower end abuts against annular shoulder 25. Thereafter, the body member 12 which is fitted with the copper spiral 13 is affixed to the transversal member 11 by pushing the locking portion 20 formed on upper body portion 18 through the bore 16 in the transversal member 11. Since the body and transversal members 12, 11 are formed of plastic material as discussed below, the enlarged locking portion 20 is deformed while passing through the bore 16 and passes therethrough until the bore 16 receives annular groove 19. It is seen that such method of attachment comprises a detachable locking or, in other words, the transversal member 11 may be removed from body portion 12. This completes the manufacture of the intrauterine contraceptive device shown in FIG. 1.

Figure 4:
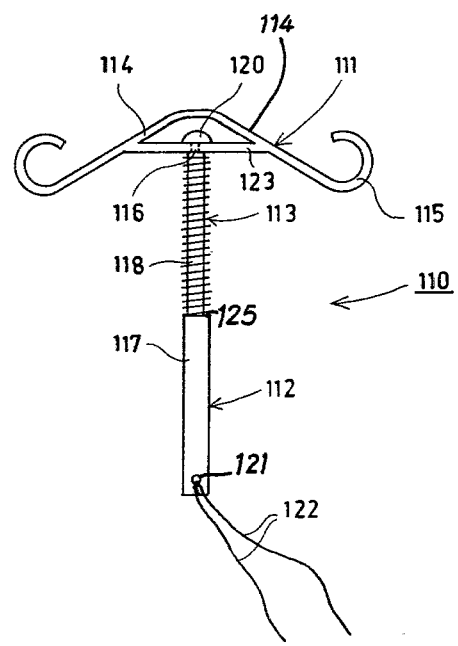
FIG. 4 is a side elevation view of another embodiment of the intrauterine contraceptive device of the present invention.
Figure 5:
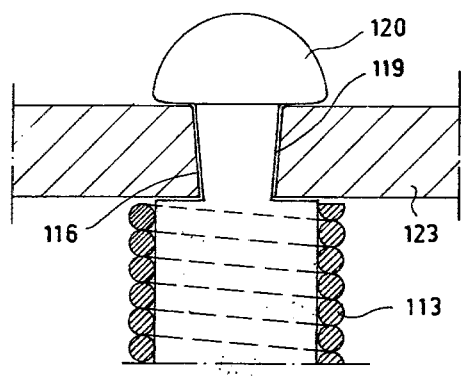
FIG. 5 is a detail view in section of the connection between the body member and the transversal member of the intrauterine contraceptive device illustrated in FIG. 4.

Referring now to FIGS. 4 and 5, another embodiment of the intrauterine contraceptive device is shown. Equivalent parts of this device are denoted by the same numerals as those used in connection with the embodiment shown in FIGS. 1 through 3 preceded by the numeral 1. Thus, the intrauterine contraceptive device 110 shown in FIG. 4 includes a body member 112 and a spiral member 113 which are identical with the corresponding elements of the FIG. 1 embodiment. Thus, body member 12 comprises a lower body portion 117 and an upper body portion 118, the helical copper member 113 being located over upper body portion 118 so that its lower end abuts against annular shoulder 115. Thin wires 122 pass through aperture 121 formed in the lower end of lower body portion 117. Referring to FIG. 5, the annular groove 119 is formed with a downwardly tapering configuration and an enlarged locking portion 120 is provided.

The transversal member 111 is defined by integrally formed leg portions 114 which terminate at their free ends in curved prong-like portions 115. However, transversal member 111 further comprises an elongate connecting member having ends each of which are integrally formed with one of the leg portions 114 thereby defining a substantially triangular space with the leg portions 114. A downwardly tapering aperture 116 is provided at the substantial midpoint of connecting member 123 so that the tapered annular groove 119 formed in the upper body portion 118, upon insertion into aperture 116, forms a reliable, detachable interlocking connection with the transversal member 111. It is seen that the connection formed by this structure is a safe, protected connection since it is located in the enclosed triangular space.

By the construction of the intrauterine contraceptive devices illustrated in FIGS. 1 and 4, it is seen that the spiral member 13, 113 is located only on the upper body portion 18, 118 of the body member 12, 112. Thus, the lower body portion 12, 112 is free of such copper member. Thus, the effect of the copper is more efficient than in the prior art devices.

Both the transversal members 11, 111 and the body members 12, 112 are formed of plastic material which is relatively flexible. Since the free ends of the transversal member 11 which comprise prong-like portions 15 are rounded, insertion of the intrauterine contraceptive device is relatively easy as is its corresponding removal since the prong-like portions 15 elastically yield both during insertion and removal.

It is advantageous in the construction of the invention to manufacture transversal members 11, 111 of a softer plastic material than the body member 12, 112 or, in other words, to form the body members 12, 112 of a relatively more rigid plastic material than transversal members 11, 111. Thus, for example, transversal member 11, 111 may be formed of LD polyethylene. Since the transversal member 11, 111 is constructed of a softer plastic material and since the configuration of the locking member 20, 120 is curved, it is readily seen that insertion of the locking member through aperture 16, 116 is facilitated. It is also seen that subsequent to locking member 20, 120 passing through aperture 16, 116, the locking member 20, 120 will snap outwardly thereby locking body member 12, 112 to transversal member 11, 111.

Obviously, numerous modification and variations of the present invention are possible in the light of the above teachings. For example, it will be obvious to one skilled in the art that the method and apparatus of the invention may be applied in the manufacture of intrauterine contraceptives of various external configurations, such for example as so-called T-shaped spirals. It is therefore to be understood that within the scope of the appended claims the invention may be practiced otherwise than is specifically described herein.

What is claimed is:

1. An intrauterine contraceptive device comprising: an elongated body member; a spiral member formed of copper disposed around said body member; a transversal member connected at its substantial midpoint to one end of said elongated body member by connecting means; and means for connecting said transversal member to said one end of said elongated body member, said connecting means comprising means for detachably connecting said transversal member to said one end of said elongated body member.

2. A device as recited in claim 1 wherein said connecting means comprises a bore formed in said transversal member and an annular groove formed at said one end of said body member.

3. A device as recited in claim 2 wherein said bore tapers downwardly and said annular groove is correspondingly tapered downwardly.

4. A device as recited in claim 1 wherein said elongated body member comprises a lower, first elongated cylindrical portion distal from said transversal member and an upper second elongated reduced diameter cylindrical portion proximate to said transversal member and wherein said spiral member is located around said second upper reduced diameter body portion.

5. A device as recited in claim 1 wherein said transversal member includes a pair of integral leg portions defining a substantially V-shaped portion and an elongate connecting member having opposed ends, each end being integrally formed with one of said leg portions, said connecting member and upper portions of said leg portions defining a triangular space therebetween, said elongated body portion being connected at said one end to said connecting member.

6. A device as recited in claim 5 wherein said connecting means comprises a bore formed in said connecting member and an annular groove formed in said one end of said body member.

7. A method of manufacturing intrauterine contraceptive devices comprising an elongate body portion, a spiral member formed of copper and a transversal portion connected at its midpoint to one end of said body portion comprising the steps of: forming a plurality of separate transversal members; forming a plurality of separate elongated body members; forming a plurality of separate copper spiral members; locating each of said separate copper spiral members around a respective separate body member; and attaching each of said separate transversal members at its midpoint to said one end of said separate body member.

8. A method as recited in claim 7 wherein said transversal member has a bore formed therethrough and said body member has an annular groove formed at said one end and having a diameter corresponding to the diameter of said bore, wherein said step of attaching comprises removably attaching said transversal member to said body portion by locating said groove within said bore.

9. A method as recited in claim 7 wherein said elongated body member comprises a first elongated cylindrical portion and a second elongated reduced diameter cylindrical portion and wherein said location of the spiral member comprises locating said spiral member around said second reduced diameter portion.

10. A method as recited in claim 7 wherein said transversal member includes a pair of integral leg portions defining a substantially V-shaped portion and an elongate connecting member having opposed ends, each end being integrally joined to one of said leg portions, said connecting member and upper portion of said leg portions defining a triangular space therebetween, said connecting step comprising connecting said body portion one end to said connecting member.

* * * * *